US00PP22719P3

(12) United States Plant Patent

LaBonte et al.

(10) Patent No.: US PP22,719 P3

(45) Date of Patent: May 8, 2012

(54) SWEETPOTATO PLANT NAMED 'BONITA'

(50) Latin Name: *Solanum tuberosum*
Varietal Denomination: Bonita

(76) Inventors: Don R. LaBonte, Baton Rouge, LA (US); Arthur Q. Villordon, Monroe, LA (US); Tara Smith, Chase, LA (US); Christopher A. Clark, Baton Rouge, LA (US)

( * ) Notice: Subject to any disclaimer, the term of this patent is extended or adjusted under 35 U.S.C. 154(b) by 0 days.

(21) Appl. No.: 12/924,725

(22) Filed: Oct. 4, 2010

(65) Prior Publication Data

US 2012/0084893 P1 Apr. 5, 2012

(51) Int. Cl.
*A01H 5/00* (2006.01)

(52) U.S. Cl. ..... Plt./258

(58) Field of Classification Search ..... Plt./258
See application file for complete search history.

(56) References Cited

OTHER PUBLICATIONS

Upov Plant Variety Database 2011/03. p. 1.*

* cited by examiner

*Primary Examiner* — Annette Para

(74) *Attorney, Agent, or Firm* — The Carver Law Firm; James C. Carver

(57) ABSTRACT

A new variety of sweetpotato identified as 'Bonita' is disclosed as having disease resistance to both southern root-knot nematode and soil rot, a white flesh, a high dry matter content, and high yield characteristics.

3 Drawing Sheets

The development of this invention was partially funded by the Government through a grant for the United States Department of Agriculture, USDA NIFA Grant Number NA/LAB93957. The Government may have certain rights in this invention.

This invention pertains to a new and distinct variety of sweetpotato.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber, "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

Genus and Species Name

This new and distinct sweetpotato variety, *Ipomoea batatas* (L.) Lam., demonstrates superior disease resistance to southern root-knot nematode, and exhibits a brighter white flesh and a drier flesh compared to the 'O'Henry' variety which represents a white flesh mutation of 'Beauregard'. It also demonstrates high yield characteristics in comparison to 'O'Henry'.

Variety Denomination

This new and distinct sweetpotato variety is identified as 'Bonita', and is characterized by a white flesh, elliptical roots, and drier flesh.

BRIEF DESCRIPTION OF THE DRAWINGS

The file of this patent contains at least one photograph executed in color. Copies of this patent or patent application with color drawing(s) will be provided by the Patent and Trademark Office upon request and payment of the necessary fee.

DETAILED BOTANICAL DESCRIPTION

This new variety of sweetpotato, named 'Bonita', resulted from an open pollinated cross performed in 1995 to the Louisiana Agricultural Experiment Station female parent 'Excel' (not patented). The male parent was unknown. Four patented male parents ('L96-117' U.S. Plant Pat. No. 15,038 P2; 'Bienville' patented U.S. Plant Pat. No. 15,380 P3; 'Evangeline' patented U.S. Plant Pat. No. 19,710P3; 'Murasaki-29' patented U.S. Plant Pat. No. 19,955 P2) were among the potential pollen sources in the crossing nursery. All patents were held by the Louisiana Agricultural Experiment Station in Baton Rouge, La. 'Bonita' was developed by the Louisiana Agricultural Experiment Station in Baton Rouge, La., to provide a variety with characteristics similar to 'O'Henry' (unpatented), but with improved resistance to southern root-knot nematode, drier flesh, higher yields, and more consistent shape. 'Bonita' was characterized by a bright white flesh with a yellow cast. The orange flesh female parent 'Excel' is unlike 'Bonita' in appearance.

Plants of 'Bonita' and 'O' Henry' can be distinguished by green vines [2.5 (green) Y (yellow) 6/6] for 'Bonita' versus green vines [7.5 G (green) Y (yellow) (5/6)] for 'O'Henry' and 'Beauregard'. Color terminology used herein is in accordance with the MUNSELL® Book of Color (Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'Bonita'.

'Bonita' roots were stored during the winter at the Louisiana Agricultural Experiment Station (Sweetpotato Research Station) in Chase, La. 'Bonita' was planted the following spring, resulting in approximately 8-10 sprouts per root. Cuttings from the sprouts were transplanted successfully for asexual reproduction. Asexual propagation of the new cultivar by cuttings has shown that the unique features of this new sweetpotato were stable and that the plant reproduced true to type in successive generations of asexual propagation. Plants described herein were approximately 90-110 days in age from planting in full sun field plantings.

Figure 1:
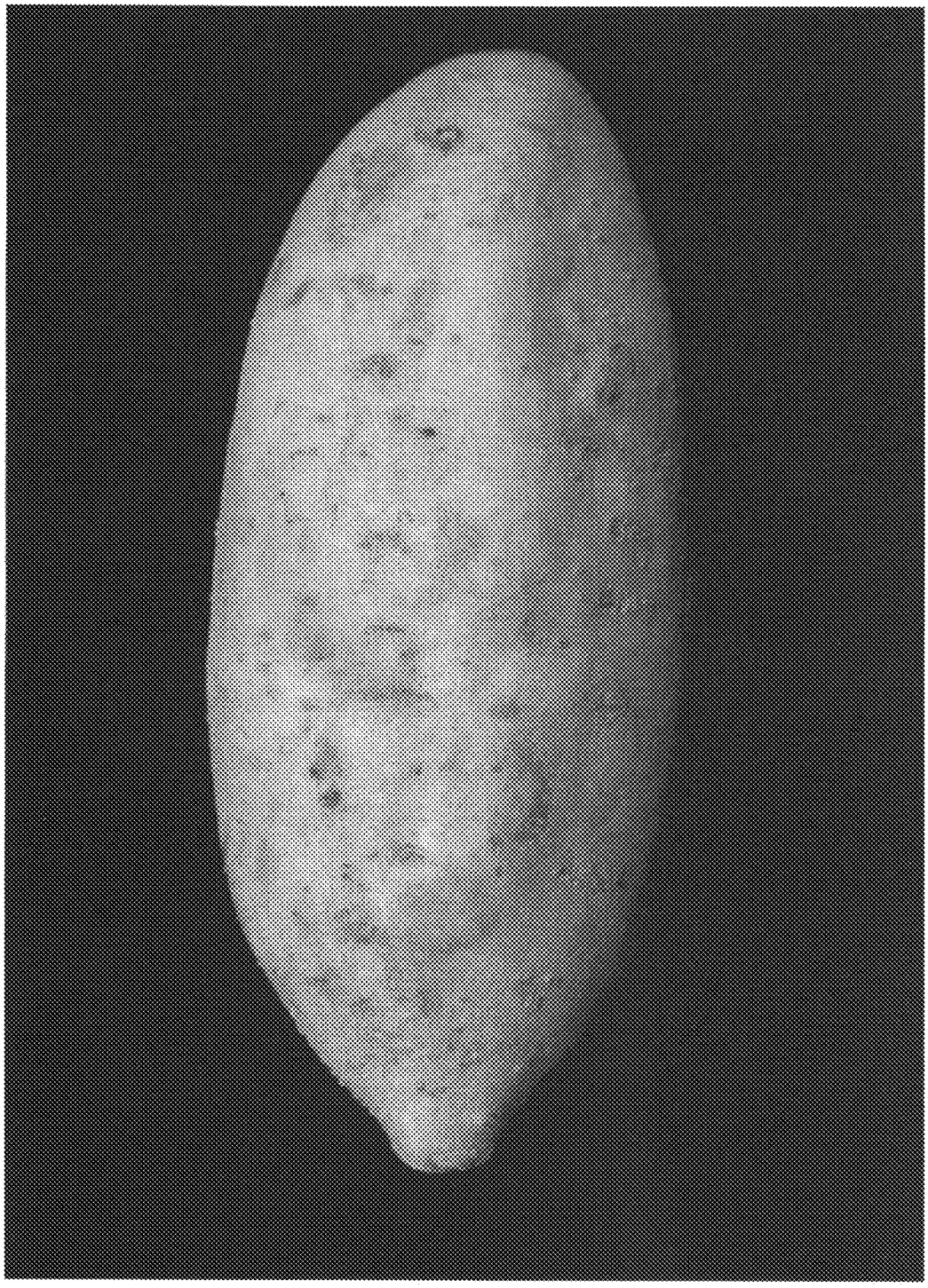
FIG. 1 is a color photograph of the fleshy root form of the novel variety of sweetpotato identified as 'Bonita'.
Figure 2:
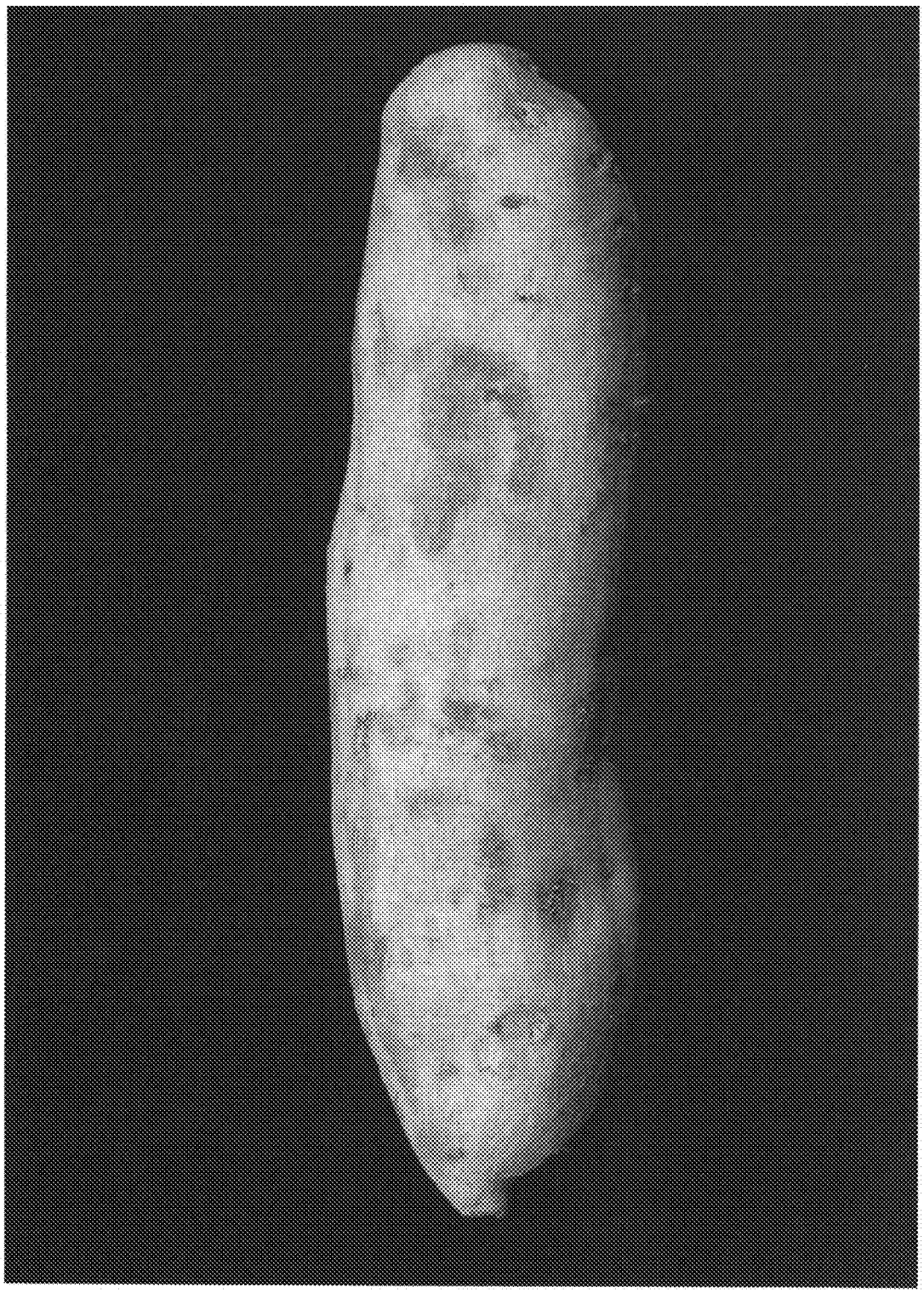
FIG. 2 is a color photograph of the fleshy root form of the sweetpotato variety identified as 'O'Henry'.

FIG. 1 depicts the fleshy root form of the 'Bonita' sweetpotato. The skin is a light tan with a pink cast which fades slightly in storage. 'O' Henry' is light tan with a yellow cast. MUNSELL® Book of Color values for skin and flesh for both 'Bonita' and 'O' Henry' storage roots after 6 months of storage are shown in Table 1. The 'O' Henry' sweetpotato is depicted in FIG. 2. The skin for both 'Bonita' and 'O' Henry' was smooth. 'Bonita' storage roots were elliptical without lobing, and they were not as long as 'O' Henry'. 'O' Henry' also has grooving along the length of the root and more prominent lenticels. The 'Bonita' cortex was 4-5 mm in depth. The flesh of 'Bonita' is a bright white with a yellow cast in comparison to 'O' Henry' which has an orange cast.

TABLE 1

| Variable | Variety | Color |
|---|---|---|
| Skin | 'Bonita' | 10Y (yellow) R (red) 8/6 |
| | 'O'Henry' | 2.5 Y (yellow) 8/6 |
| Flesh | 'Bonita' | 7.5 Y (yellow) 9/4 |
| | 'O'Henry' | 5 Y (yellow) 9/4 |

Figure 3:
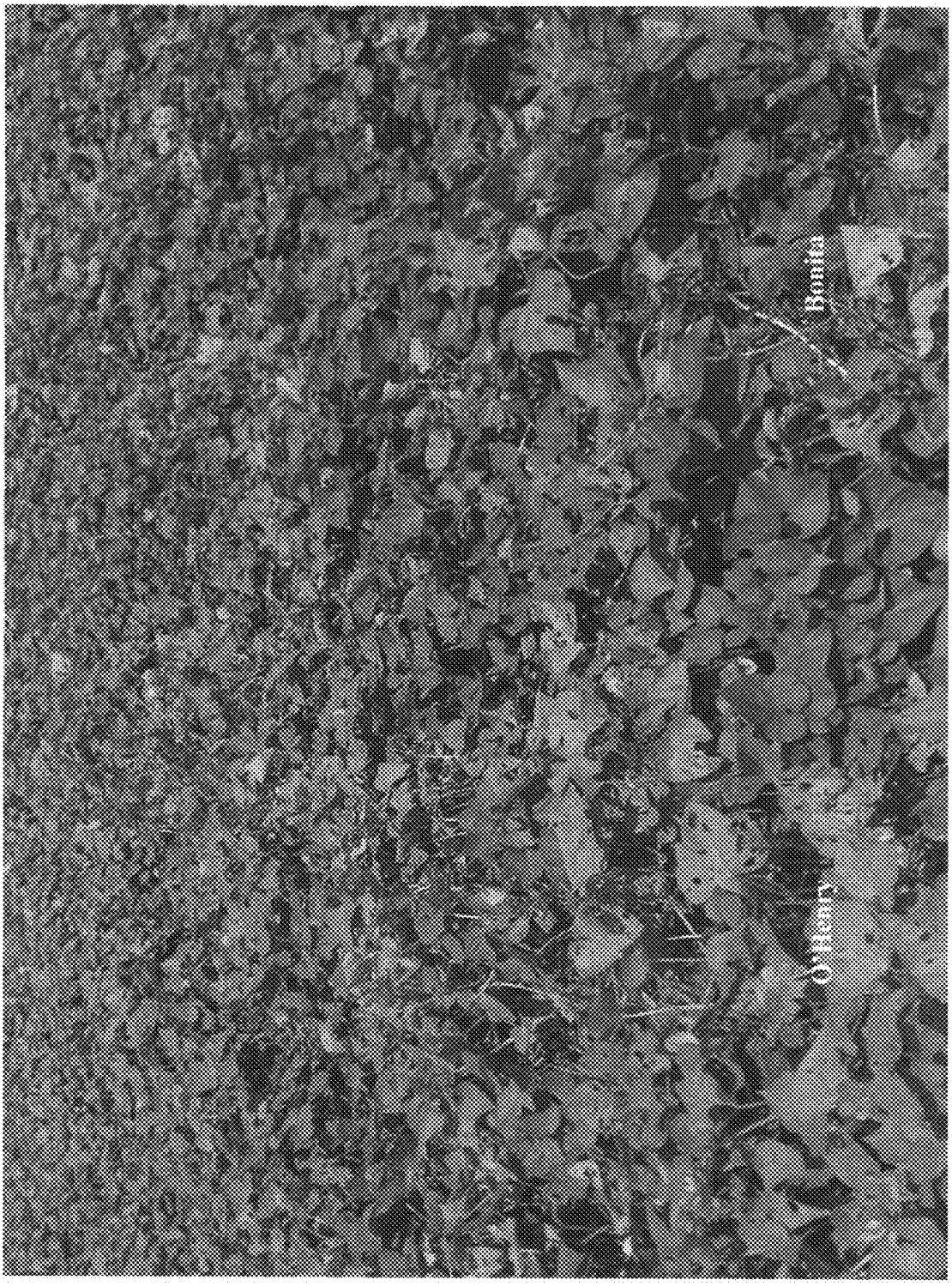
FIG. 3 is a color photograph of the canopy biomasses of the novel variety of sweetpotato identified as 'O'Henry' (shown on the left side of the photograph) and the variety identified as 'Bonita' (shown on the right side of the photograph).

FIG. 3 depicts the canopy biomass of both 'Bonita' sweetpotatoes and 'O' Henry' sweetpotatoes. 'Bonita' has green-stemmed vines [2.5 G (green) Y (yellow) (6/6)] from the apex and then transitions to a dark maroon [5 R (red) (3/2)] on older parts of the vines near the crown of the roots. The 'Bonita' canopy biomass appears to be greater than that for 'O' Henry'. The 'Bonita' canopy architecture was upright (28 cm in height from the soil surface) and erect prior to spreading (365 cm radius), while 'O' Henry' exhibited a prostrate growth habit (21-22 cm in height from the soil surface). For 'Bonita', three to four main vines arose from the main stem near the soil surface. The stem giving rise to these vines was 2.0 cm in diameter; the 3-4 lateral vines were 180 cm in length with diameters of about 0.6 cm at 65 cm from the base, diameters of about 0.7 cm at the base of the vine, and diameters of about 0.6 cm at the first internode of the first fully developed leaf from the apex. Four to five lateral branches arose from each of the main vines. At the first internode from the apex, the internode length was about 3.5 cm between the first and second fully developed leaves. Internode lengths for other sections of the vine averaged about 4.7 cm. Unfolded immature leaves were green [2.5 G(green) Y (yellow) (5/4)] for the upper and lower surface, which changed slightly over one to two nodes from the upper surface [7.5 G (green) Y (yellow) (3/4)] to light green lower surface [5 G (green) Y (yellow) (4/6)]. Mature leaves at five nodes from the apex had an acute apex and mostly a cordate base and a smooth leaf margin. Mature leaves were about 10.6 cm long and 10.3 cm wide. Abaxial and adaxial veins were green [5 G (green) Y (yellow) (5/8)]. There is a blending of adaxial vein coloration from the red petiole [5 R (red) (3/6)] junction for about the first 0.8 cm before becoming green at its junction with the leaf, which quickly changed to green [5 G (green) Y (yellow) (5/8)]. The petiole was 17 cm long at five nodes from the apex, and 3-4 mm in diameter at 5 cm from the leaf junction. The dormant nodal meristem also was green [5 G (green) Y (yellow) (4/6)]. Adaxial veins of 'O' Henry' have no red hues and are green [2.5 G (green) Y (yellow)].

A typical inflorescence of 'Bonita' displayed three flowers per peduncle. Peduncles were green [2.5 G (green) Y (yellow) (6/10)], about 3 cm long, and about 2.3 mm in diameter. Individual flowers were about 4 cm long from the base of the calyx, and the corolla was 3 cm wide at the opening. The fused flower petals formed a pentagonal pattern with smooth edges. The inner throat of the corolla appeared purple [2.5 R (red) P (purple) (3/8)]. The inner and outer limbs of the corolla (corollas outermost area, distal from the calyx) were very light purple [5 P (purple) (9/2)]. The five sepals comprising the calyx were elliptic with a cordate apex and appeared to be green [2.5 G (green) Y (yellow) (6/10)]; three of these sepals were about 11 mm long and 5 mm wide. Two other sepals (interspersed) were about 9 mm wide. Sepal margins were smooth. Stigmata were about 1.2 cm long and appeared to be purple [7.5 R (red) P (purple) (7/8)]. Four of the five stamens were inferior to stigmata; one is slightly superior. No fragrance was present.

EXAMPLE 1

Tests Conducted

To confirm that 'Bonita' was a new variety, controlled tests (e.g., pathogen responses and yield) were conducted at the Louisiana Agricultural Experiment Station in Baton Rouge, La. 'Beauregard' was selected for comparison because of its importance in commercial United States orange flesh sweetpotato acreage. 'O'Henry' is assumed to react similarly, but it has not been tested. Diseases that commonly affect the growth of sweetpotatoes were selected to test for pathogen responses in both varieties. Scions of 'Bonita' and 'Beauregard' reacted similarly to most diseases evaluated in the controlled tests. 'Bonita' and 'Beauregard' were intermediate to resistant for soil rot caused by *Streptomyces ipomoeae* (Person & W. J. Martin) Waksman & Henrici. 'Bonita' is slightly less resistant than 'Beauregard' to Fusarium wilt or stem rot caused by *Fusarium oxysporum* Schlect. f. sp. *batatas* (Wollenw.) Snyd. & Hans.

Nematode reproduction was measured in greenhouse tests. 'Bonita' was resistant to southern root-knot nematode, *Meloidogyne incognita* (Kofoid & White 1919) Chitwood 1949. 'Beauregard' was susceptible to southern root-knot nematode. 'Bonita' was susceptible to *Rhizopus* soft rot caused by *Rhizopus stolonifer* (Ehr. ex. Fr.) Lind while 'Beauregard' was resistant.

'Bonita' did not appear to show any novel insect resistance.

To determine yield production, complete-block trials using four replications of 'Bonita' and 'O' Henry' each were conducted in 2008 and 2009 in areas of Louisiana, Mississippi, and Alabama likely to produce 'Bonita'. 'Bonita' and 'O 'Henry' sweetpotato plants were transplanted in randomized complete-block trials at 31 cm spacings. Each block/plot was fertilized with approximately 250 pounds per acre of a mixed fertilizer comprising 13% N, 13% $P_2O_5$, and 13% $K_2O$. 'Bonita' was compared to 'O' Henry' at transplanting dates beginning in May-June. Average yields were measured for the following grades of roots: U.S. #1 (51-89 mm in diameter, 76-229 mm long); Canner (25-51 mm in diameter, 51-178 mm long); and Jumbo (larger than U.S. #1 in diameter, length or both, and without objectionable defects). A typical marketable root of 'Bonita' was 180-190 mm long, 60-70 mm in diameter, with mostly round-elliptic in shapes. The base or distal end tended to be more elongated in comparison to slightly rounder apex (proximal end). U.S. #1 roots typically weighed 150-190 g.

The early transplanting date trial was conducted at Wisner, La. in 2008. 'Bonita' and 'O' Henry' were transplanted on May 27, 2008, and harvested on Sep. 23, 2008 (119 days after planting). Average yields, measured as Metric Tons per Hectare ("$MT \cdot ha^{-1}$), are shown in Table 2.

TABLE 2

| Selection | US#1† | Canners† | Jumbos† | TMY‡† |
|---|---|---|---|---|
| 'Bonita' | 22.69a | 8.52a | 6.56a | 37.82a |
| 'O'Henry' | 19.49a | 9.58a | 0.84a | 29.86a |

†Average yields in $MT\text{-}ha^{-1}$ of varieties followed by a common letter do not differ significantly ($P < 0.05$) according to Duncan's Multiple Range Test.
TMY‡ = total marketable yield A second transplanting date trial was also conducted at Foley, Ala. on May 2, 2009, and harvested on Sep. 21, 2009 (123 days after planting). Average yields ($MT \cdot ha^{-1}$) by grade of 'Bonita' and 'O' Henry' are shown in Table 3.

TABLE 3

| Selection | US#1† | Canners† | Jumbos† | TMY‡† |
|---|---|---|---|---|
| 'Bonita' | 28.30a | 13.56a | 1.63a | 43.42a |
| 'O'Henry' | 16.24a | 16.36a | 1.23a | 34.01b |

†Average yields in $MT\text{-}ha^{-1}$ of varieties followed by a common letter do not differ significantly ($P < 0.05$) according to Duncan's Multiple Range Test.
TMY‡ = total marketable yield A late transplanting date trial was also conducted at Bonita, La. on Jun. 29, 2009, and harvested on Nov. 11, 2009 (136 days after planting). Average yields ($MT \cdot ha^{-1}$) by grade of 'Bonita' and 'O' Henry' are shown in Table 4.

TABLE 4

| Selection | US#1† | Canners† | Jumbos† | TMY‡† |
|---|---|---|---|---|
| 'Bonita' | 26.67a | 17.76a | 0a | 44.49a |
| 'O'Henry' | 18.27b | 19.78a | 0a | 38.10a |

†Average yields in $MT\text{-}ha^{-1}$ of varieties followed by a common letter do not differ significantly ($P < 0.05$) according to Duncan's Multiple Range Test.
TMY‡ = total marketable yield An early-season transplanting date trial was also conducted at Vardaman, Miss. on Jun. 3, 2009, and harvested on Oct. 1, 2009 (120 days after planting). Average yields ($MT \cdot ha^{-1}$) by grade of 'Bonita' and 'O' Henry' are shown in Table 5.

TABLE 5

| Selection | US#1† | Canners† | Jumbos† | TMY‡† |
|---|---|---|---|---|
| 'Bonita' | 19.39a | 21.63a | 1.79a | 50.32a |
| 'O'Henry' | 19.27a | 15.68a | 3.02a | 40.40b |

†Average yields in $MT\text{-}ha^{-1}$ of varieties followed by a common letter do not differ significantly ($P < 0.05$) according to Duncan's Multiple Range Test.
TMY‡ = total marketable yield As shown in Tables 2-5, 'Bonita' produced yields comparable to, and exceeding 'O' Henry' in regional trials at various planting dates. Trials in sandy loams (Tables 3 and 4) showed 'Bonita' had a higher yield of U.S. # 1 grade in comparison to 'O 'Henry'. Yield in heavier silt loam soils were more comparable (Tables 1, 2, and 5). Replicated plots at other farms and on station have shown 'Bonita' has consistent yields for early, middle, or late season plantings. Yield declines are within norms in poor environments. 'Bonita' had harvestable roots approximately 110-115 days after planting, which is typical development time for sweetpotatoes and comparable to 'O' Henry'. The yield of Jumbo grade is indicative of earliness and 'Bonita' might produce more jumbo roots under ideal conditions. White fleshed jumbo roots have a low economic value. In National Sweet Potato Collaborator trials, yield of 'Bonita' for U.S. #1 grade exceeded 'O' Henry' by over 10% in 2009 in two trials in North Carolina, the largest U.S. production region for sweetpotato. Yield in nine other plots in Louisiana in years 2006, 2007, and 2008 showed no significant difference in yield in comparison to the high yield 'Beauregard' variety. Yield of 'Bonita' was significantly higher in one plot in 2007 in comparison to 'Beauregard'. In total, this data reflects consistent high yield characteristics for 'Bonita'.

Sugar profiles for baked 'Bonita' and 'O'Henry' are shown in Table 6. For this 2009 test, roots were stored for five months after which they were baked at 190° C. for approximately 2.0 h. Sucrose content in baked 'Bonita' was twice that found in baked 'O'Henry'. 'Bonita' and 'O'Henry' had similar maltose content. Total sugar content was slightly higher for 'Bonita' in comparison to 'O'Henry'. 'Bonita' exhibited a greater sugar profile than 'O'Henry' sweetpotatoes. A high dry matter of 28.6% makes for a drier, flaky texture in comparison to 'O' Henry' at 24.5%.

TABLE 6

| Selection | Fructose‡ | Glucose‡ | Sucrose‡ | Maltose‡ | Total sugars†‡ |
|---|---|---|---|---|---|
| 'Bonita' | 0.76 (2009) | 0.96 (2009) | 2.92 (2009) | 8.41 (2009) | 13.05 (2009) |
| 'O'Henry' | 1.22 (2009) | 1.57 (2009) | 1.30 (2009) | 7.31 (2009) | 11.40 (2009) |

†Total sugars = fructose + glucose + maltose + sucrose.
‡$mg \cdot g^{-1}$ = fresh weight basis.

'Bonita' should be a valuable commercial sweetpotato variety. 'Bonita' produced plants (sprouts) comparable to 'O' Henry'. Days to harvest for 'Bonita' were similar to 'O' Henry'. 'Bonita' exhibited superior flesh color, smoother root surface, and a drier, sweeter flesh. 'Bonita' is ideally suited for production on land infested with southern root-knot nematode and soil rot.

We claim:

1. A new and distinct variety of *Ipomoea batatas* plant named 'Bonita' as described and illustrated in the specification herein.

* * * * *

UNITED STATES PATENT AND TRADEMARK OFFICE

CERTIFICATE OF CORRECTION

PATENT NO. : PP22,719 P3
APPLICATION NO. : 12/924725
DATED : May 8, 2012
INVENTOR(S) : Don R. LaBonte et al.

It is certified that error appears in the above-identified patent and that said Letters Patent is hereby corrected as shown below:

Front Page, Left Column, Item (50) Latin Name: reads "Solanum tuberosum," and should read "Ipomoea batatas."

Signed and Sealed this
Twenty-eighth Day of August, 2012

David J. Kappos

David J. Kappos
*Director of the United States Patent and Trademark Office*